US012508169B2

(12) United States Patent
Cocozzella et al.

(10) Patent No.: US 12,508,169 B2
(45) Date of Patent: Dec. 30, 2025

(54) APPARATUS FOR TREATING CONTINUOUS MOVING WEBS AND A MACHINE COMPRISING THIS APPARATUS

(71) Applicant: Fameccanica.Data S.p.A., San Giovanni Teatino Chieti (IT)

(72) Inventors: Nicola Cocozzella, San Giovanni Teatino Chieti (IT); Davide Sepe, San Giovanni Teatino Chieti (IT)

(73) Assignee: Fameccanica.Data S.p.A., San Giovanni Teatino Chieti (IT)

( * ) Notice: Subject to any disclaimer, the term of this patent is extended or adjusted under 35 U.S.C. 154(b) by 0 days.

(21) Appl. No.: 18/967,963

(22) Filed: Dec. 4, 2024

(65) Prior Publication Data

US 2025/0177215 A1 Jun. 5, 2025

(30) Foreign Application Priority Data

Dec. 5, 2023 (IT) ........................ 102023000025977

(51) Int. Cl.
*A61F 13/00* (2024.01)
*A61F 13/15* (2006.01)

(52) U.S. Cl.
CPC .. *A61F 13/15772* (2013.01); *A61F 13/15699* (2013.01); *A61F 13/15723* (2013.01); *A61F 13/15731* (2013.01); *A61F 2013/15796* (2013.01)

(58) Field of Classification Search
CPC .......... A61F 13/15772; A61F 13/15699; A61F 13/15723; A61F 13/15731; A61F 2013/15796
USPC .......................................................... 493/394
See application file for complete search history.

(56) References Cited

U.S. PATENT DOCUMENTS

2012/0247661 A1* 10/2012 Ogasawara ............ B65H 35/08 156/256
2023/0150159 A1* 5/2023 Lupinetti ............... B26D 1/265 83/602
2023/0234254 A1* 7/2023 Bittner ................. B26D 7/2628

OTHER PUBLICATIONS

Search Report dated May 8, 2024. 6 pages.

* cited by examiner

*Primary Examiner* — Jacob A Smith
(74) *Attorney, Agent, or Firm* — RMCK Law Group PLC

(57) ABSTRACT

An apparatus for treating a moving continuous web includes a tool holder roller, an anvil roller and a control device configured to rotate the tool holder roller and the anvil roller around respective rotation axes in at least one first operating condition and one second operating condition, so as to carry out a change of format of the apparatus with a selection via software.

10 Claims, 3 Drawing Sheets

APPARATUS FOR TREATING CONTINUOUS MOVING WEBS AND A MACHINE COMPRISING THIS APPARATUS

CROSS-REFERENCE TO RELATED APPLICATION

This application claims priority to Italian Patent Application No. 102023000025977 filed Dec. 5, 2023. The disclosure of the above application is incorporated herein by reference in its entirety.

FIELD OF THE INVENTION

The present invention relates in general to treating continuous moving webs.

More specifically, the invention relates to an apparatus that can be used to perform operations of cutting, welding, embossing, drilling, etc. on continuous moving webs, for example, on composite webs comprising one or more non-woven layers.

The invention was developed in particular for its application to producing absorbent sanitary articles, such as diapers, diaper-pants, absorbent articles for incontinent adults, etc., but is not limited to this specific sector.

According to another aspect, the invention concerns a machine comprising an apparatus for treating continuous moving webs.

DESCRIPTION OF THE PRIOR ART

For producing absorbent sanitary articles, it is frequently necessary to carry out various types of webs, for example, processing on continuous moving continuous composite webs comprising a plurality of elastic threads enclosed between one or more non-woven layers. Processing operations may comprise, for example, cutting, welding, embossing, drilling, etc.

These operations are normally carried out using an apparatus comprising an anvil roller and a tool holder roller on which tools such as cutting blades, welding elements, embossing elements, etc. are arranged depending on the processing operations to be carried out.

Rotary machines for treating continuous moving webs are configured to operate on webs corresponding to a specific format of absorbent sanitary articles.

When the format of the absorbent sanitary articles produced on the same line changes, the width of the operations that must be carried out on the continuous webs used for producing absorbent sanitary articles often also changes.

Normally, when the format of the absorbent sanitary articles changes, the rotary tools that perform the operations of cutting, welding, embossing, etc. must be replaced to adapt the width of the tools to the new size of the articles to be produced.

The solutions currently adopted to carry out a format change involve the complete or partial replacement of the rotary unit.

Changing the format is one of the most complex and time-consuming activities, as it requires disengagement of the rotary axes transmissions, pneumatic connections and mechanical fastenings of the unit, in particularly difficult-to-reach points.

Furthermore, extraction of the unit requires that there is access space in the line for a lifting device such as a forklift truck, which severely limits the possibilities for using the space in front of the machine.

In some cases, it may be necessary to replace only the tool holder roller of the apparatus, but this also involves the need to carry out very delicate adjustment operations (in the order of microns), which may lead to the risk of damaging the tools.

OBJECT AND SUMMARY OF THE INVENTION

The object of the present invention is to provide an apparatus for treating continuous moving webs that overcomes the problems of the prior art According to the present invention, this object is achieved by an apparatus having the characteristics of claim 1.

According to another aspect, the invention relates to a machine according to claim 10.

Preferred embodiments of the invention form the subject of the dependent claims.

The claims form an integral part of the disclosure provided here in relation to the invention.

BRIEF DESCRIPTION OF THE DRAWINGS

The present invention will now be described in detail with reference to the attached drawings, given purely by way of non-limiting example, wherein.

DETAILED DESCRIPTION

Figure 2:
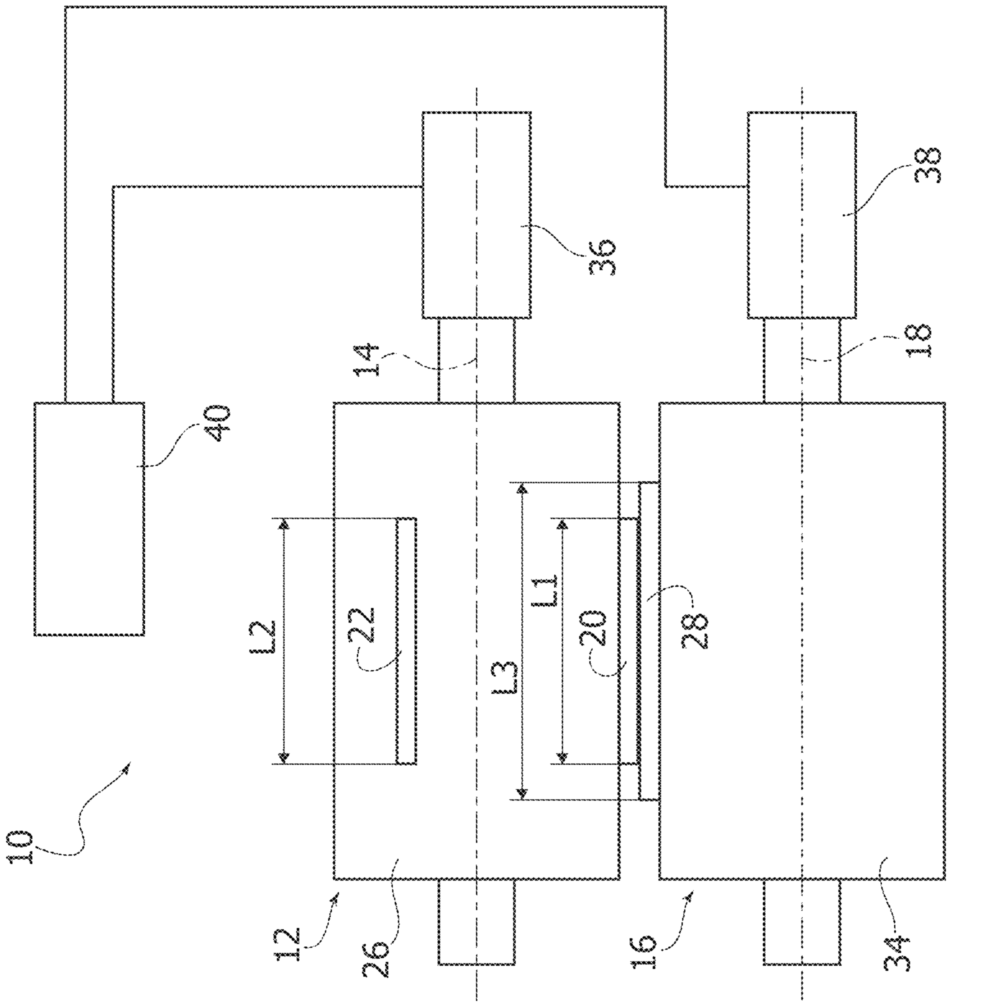
FIG. 2 is a schematic side view according to the arrow II of FIG. 1.

With reference to FIGS. 1-4, numeral 10 indicates an apparatus for treating a continuous moving web.

The apparatus 10 comprises a tool holder roller 12 rotatable around a first rotation axis 14 and an anvil roller 16 rotatable around a second rotation axis 18 parallel to the first rotation axis 14.

The tool holder roller 12 carries at least one first tool 20 and at least one second tool 22 spaced angularly apart from each other. In general, the tool holder roller 12 may carry a generic number of tools equal to or greater than 2. In the example illustrated in the Figures, the tool holder roller 12 carries a first tool 20, a second tool 22 and a third tool 24.

Below reference will be made, by way of example, to the case wherein the tool holder roller 12 carries a first tool 20 and a second tool 22, but it is understood that what will be described applies equally to the case wherein the tool holder roller 12 carries a generic number of tools equal to or greater than 2.

The first tool 20 and the second tool 22 may be configured to perform an operation chosen from: cutting, welding, embossing, laminating, and perforating.

The first tool 20 and the second tool 22 have different geometric characteristics. In particular, the first tool 20 and the second tool 22 may have respective different lengths L1, L2.

The first tool 20 and the second tool 22 may have active surfaces configured to perform different processing operations, for example, the same type of machining but with different patterns or different processing operations, e.g. welding, embossing, etc.

In possible embodiments, the first tool 20 and the second tool 22 protrude radially from an outer surface 26 of the tool holder roller.

The anvil roller 16 carries at least one anvil element 28.

Figure 1:
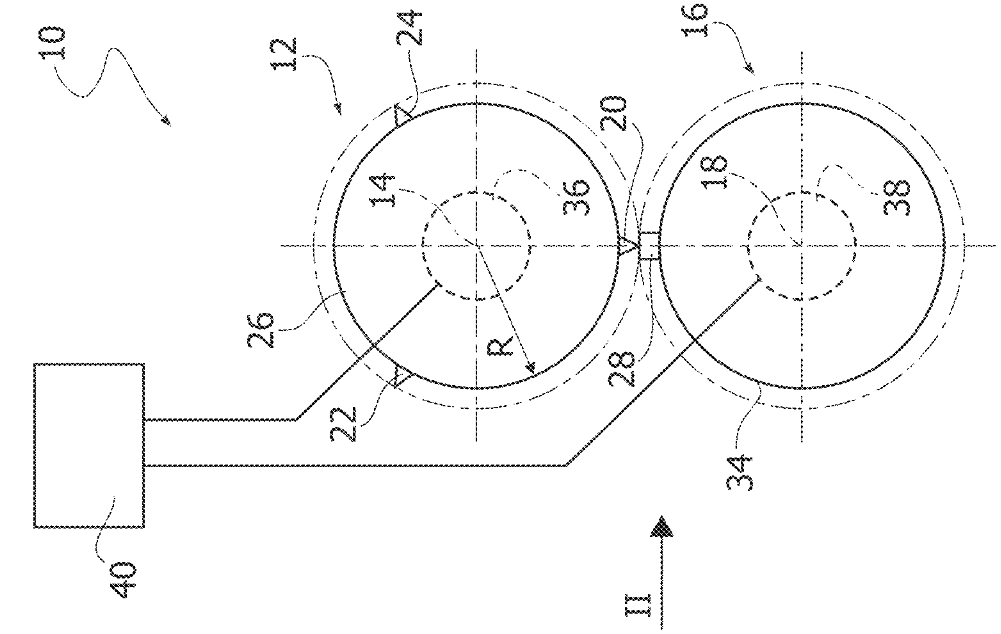
FIG. 1 is a schematic front view of a first embodiment of an apparatus according to the present invention.

In the embodiment illustrated in FIGS. 1 and 2 the anvil roller 16 carries a single anvil element 28. In this case, as will be described below, the first tool 20, the second tool 22 and any additional tools 24 are intended to cooperate with the same anvil element 28. The single anvil element 28 has a width L3 greater than the maximum width of the tools 20, 22, 24.

Figure 4:
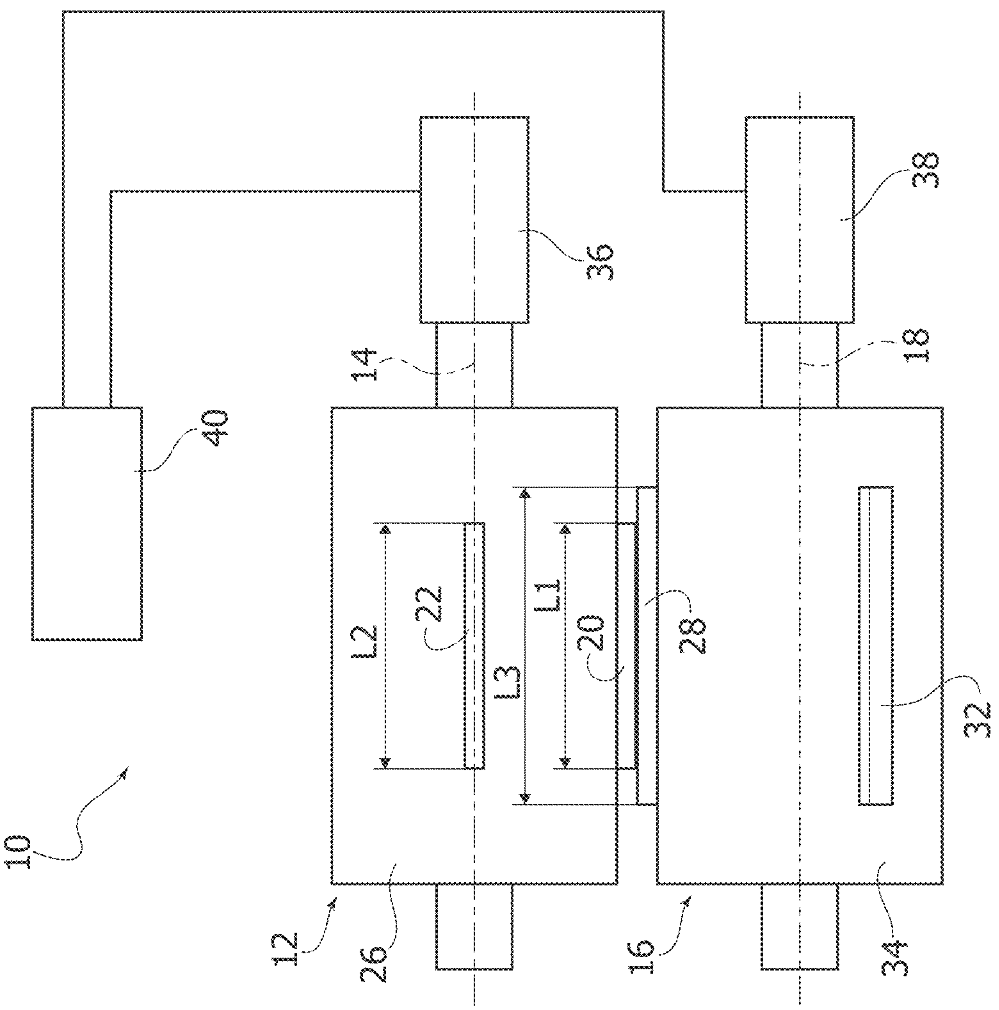
FIG. 4 is a schematic side view according to the arrow IV of FIG. 2, and FIGS. 5 and 6 are schematic plan views of two continuous webs processed by an apparatus according to the present invention in a first operating condition and in a second operating condition, respectively.
Figure 3:
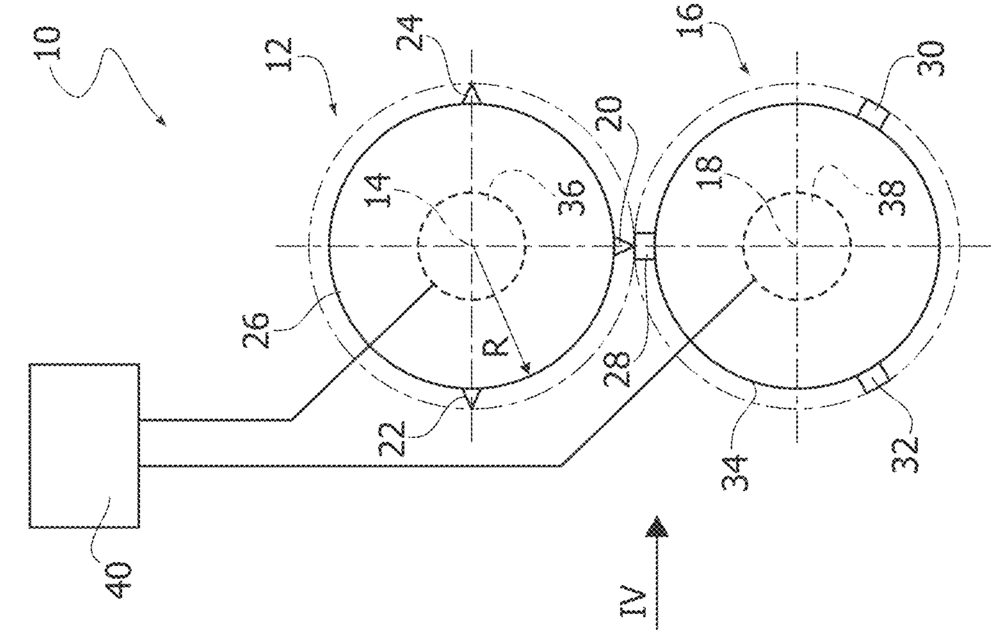
FIG. 3 is a schematic front view of a second embodiment of an apparatus according to the present invention.

In the embodiment illustrated in FIGS. 3 and 4 the anvil roller 16 carries a plurality of anvil elements 28, 30, 32 spaced angularly apart from each other. In this case, as will be described below, the first tool 20, the second tool 22 and any additional tools 24 are intended to cooperate with respective anvil elements 28, 30, 32. In this case each tool 20, 22, 24 may be set with the corresponding anvil element 28, 30, 32.

Each of the anvil elements 28, 30, 32 may protrude radially from an outer surface 34 of the anvil roller 16.

The tool holder roller 12 and the anvil roller 16 are driven by respective electric motors 36, 38 controlled by a control device 40.

The control device 40 is configured to rotate the tool holder roller 12 and the anvil roller 16 about their respective rotation axes 14, 18 in at least one first and one second operating condition. The number of operating conditions may be equal to the number of different tools 20, 22, 24 provided on the tool holder roller 12.

In the first operating condition, the first tool 20 of the tool holder roller 12 is in phase with the single anvil element 28 or with a respective anvil element 28, 30, 32 and, during operation, it cooperates cyclically with the single anvil element 28 or with a respective anvil element 28, 30, 32 to carry out a processing operation on a continuously moving web. In the first operating condition, the second tool 22 and any additional tool 24 are out of phase with respect to the single anvil element 28 or with respect to the plurality of anvil elements 28, 30, 32 and, during operation, do not cooperate with any anvil element 28, 30, 32. In the second operating condition, the second tool 22 of the tool holder roller 12 is in phase with the single anvil element 28 or with a respective anvil element 28, 30, 32 and, during operation, it cooperates cyclically with the single anvil element 28 or with a respective anvil element 28, 30, 32 to carry out a processing operation on a continuously moving web. In the second operating condition, the first tool 20 and any additional tool 24 are out of phase with respect to the single anvil element 28 or with respect to the plurality of anvil elements 28, 30, 32 and, during operation, do not cooperate with any anvil element 28, 30, 32.

Therefore, the apparatus 10 may operate in different operating conditions in each of which only one type of tool is operational and may switch from one operating condition to another with a software selection.

The transition from one operating condition to another gives the possibility of changing the geometry of the processing carried out on a continuous moving web and corresponds to a change in format of the apparatus 10.

Figure 5:
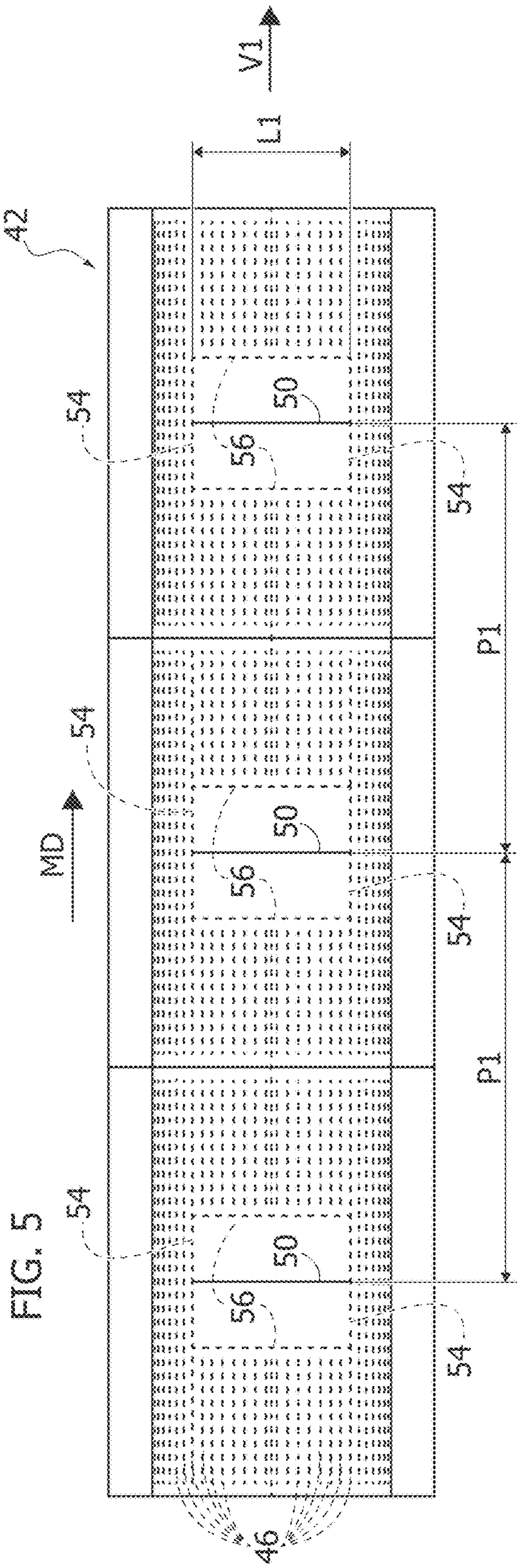
Figure 6:
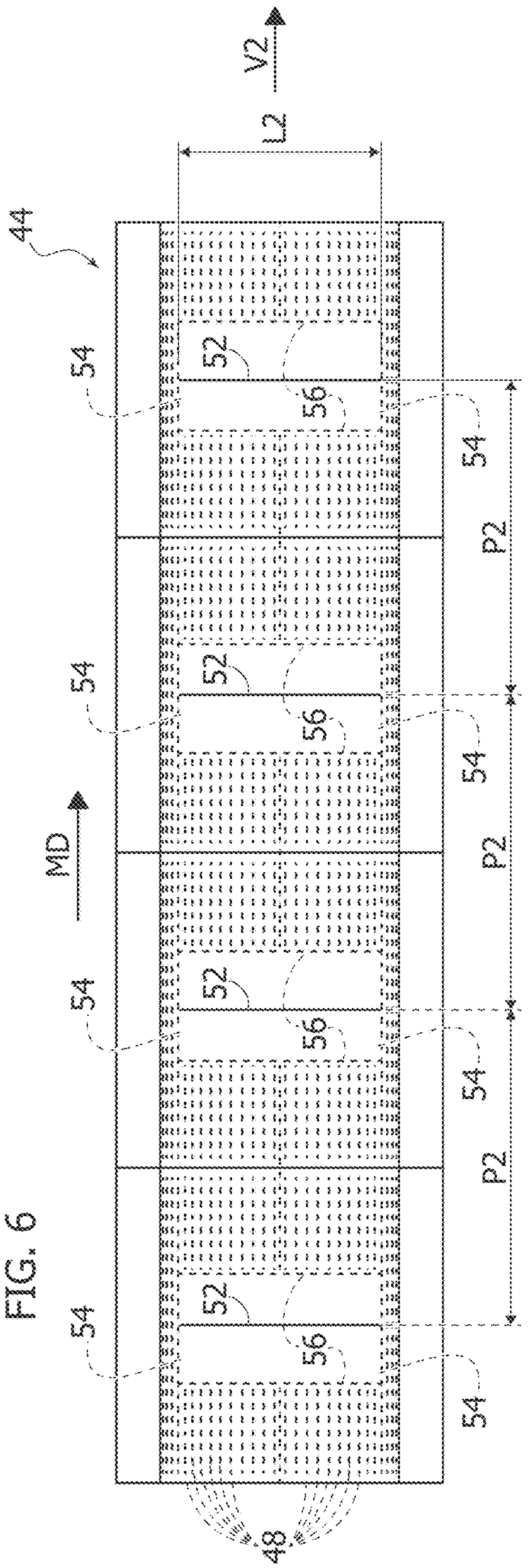

FIGS. 5 and 6 show two continuous webs 42, 44 processed by the apparatus 10 in the first and second operating conditions, respectively. In the example illustrated, the continuous webs 42, 44 are elastic bands comprising a plurality of longitudinal elastic threads 46, 48 enclosed between two non-woven layers. The longitudinal elastic threads 46, 48 are attached between the two continuous webs 42, 44 by means of discontinuously applied adhesive. Lines 54 and 56 define windows in which no adhesive is applied and in which the longitudinal elastic threads 46, 48 are not attached between the two continuous webs 42, 44.

In the illustrated example, the continuous webs 42, 44 are subjected to cutting operations in the apparatus 10 to cut the longitudinal elastic threads 46, 48 transversely at regular intervals. In FIGS. 5 and 6 the transverse cuts are indicated with 50 and 52 and have respective widths L1 and L2. After the transverse cuts 50, 52, the longitudinal elastic threads 46, 48 in the sections wherein they are not attached to the two continuous webs 42, 44 retract to the respective lines 56.

In the first operating condition, the apparatus 10 is configured to operate with a first tool 20 having a width L1, which cooperates cyclically with one of the anvil elements 28, 30, 32 to carry out first cuts 50 on the first moving continuous web 42 with width L1 and with a pitch P1.

In the second operating condition, the apparatus 10 is configured to operate with a second tool 22 having a width L2, which cooperates cyclically with one of the anvil elements 28, 30, 32 to carry out second cuts 52 on the second moving continuous web 44 with width L2 and with a pitch P2.

The change of operating conditions is done exclusively via software, without the need to replace components and without the need to make settings or adjustments.

The control device 40 controls the tool holder roller 12 and the anvil roller 16 in phase with each other so as to carry out the operations, in this case the cuts 50 or 52, with the required pitches P1, P2.

The rotation speeds of the tool holder roller 12 and the anvil roller 16 may vary during each single rotation to carry out operations with programmed pitches P1, P2.

When the tool 20, 22, 24, which is operational at any given time, cooperates with a respective anvil element 28, 30, 32, the speeds of the tool 20, 22, 24 and of the anvil element 28, 30, 32 may be equal to the feed rate V1, V2 of the continuous web 42, 44 in the machine direction MD. After having performed an operation, the tool 20, 22, 24 operating at any given time and the respective anvil element 28, 30, 32 may accelerate or decelerate to perform the next operation after the continuous web 42, 44 has advanced in the machine direction MD by a pre-established pitch P1, P2. The tools that are not operational contact the continuous web 42, 44 out of phase with respect to the anvil elements 28, 30, 32 and do not perform any operation on the web 42, 44.

The apparatus 10 may be configured to carry out intermittent operations on the moving continuous webs 42, 44 having respective extensions in the longitudinal direction of the continuous webs 42, 44.

Each operation has an extension in the direction of movement of the web (machine direction MD) that is less than the size of the circumference of the anvil roller 12 divided by the number of possible format changes. For example, if the anvil roller 12 has a radius R and carries n tools, each operation may have a dimension in the machine direction MD less than $2\pi R/n$.

It will be understood that it is possible to combine multiple apparatuses 10 to perform different operations or the same operation with different widths.

The invention also relates to a machine for producing absorbent sanitary articles, such as diapers, diaper-pants, absorbent articles for incontinent adults, etc. comprising an apparatus for treating continuous moving webs as previously described.

Of course, without prejudice to the principle of the invention, the details of construction and the embodiments can be widely varied with respect to those described and illustrated, without thereby departing from the scope of the invention as defined by the claims that follow.

The invention claimed is:

1. An apparatus for treating a continuous moving web, comprising:

a tool holder roller rotatable around a first rotation axis and carrying at least one first tool and at least one second tool spaced angularly apart from each other and having geometric characteristics different from each other, an anvil roller rotatable around a second rotation axis parallel to the first rotation axis and carrying at least one anvil element, and a control device configured to rotate the tool holder roller and the anvil roller around the respective rotation axes in at least one first operating condition and at least one second operating condition, wherein in the at least one first operating condition said at least one first tool is in phase and cooperates cyclically with the at least one anvil element and said at least one second tool is out of phase and does not cooperate with the at least one anvil element, and wherein in the at least one second operating condition said at least one second tool is in phase and cooperates cyclically with the at least one anvil element and said at least one first tool is out of phase and does not cooperate with the at least one anvil element.

2. The apparatus of claim 1, wherein said at least one first tool and at least one second tool have respective lengths different from each other.

3. The apparatus of claim 1, wherein said at least one first tool and said at least one second tool are configured to perform operations selected from: cutting, welding, laminating, embossing, and perforating.

4. The apparatus of claim 1, wherein said at least one first tool and said at least one second tool have respective active surfaces configured to perform operations different from each other.

5. The apparatus of claim 1, wherein said at least one first tool and said at least one second tool in said at least one first and second operating conditions cooperate with a same anvil element of the at least one anvil element.

6. The apparatus of claim 1, wherein the at least one anvil element includes a plurality of anvil elements, wherein the anvil roller carries the plurality of anvil elements spaced angularly apart from each other, and wherein in said at least one first and second operating conditions said at least one first tool and said at least one second tool cooperate with respective anvil elements of the plurality of anvil elements.

7. The apparatus of claim 1, wherein said at least one first tool and said at least one second tool protrude in a radial direction from an outer surface of the tool holder roller.

8. The apparatus of claim 1, wherein said at least one anvil element protrudes in a radial direction from an outer surface of the anvil roller.

9. The apparatus of claim 1, wherein said control device is configured to vary rotation speeds of the tool holder roller and the anvil roller during each single rotation to carry out operations with programmed pitches.

10. A machine comprising the apparatus for treating the continuous moving web as claimed in claim 1.

* * * * *